United States Patent [19]

Anthony

[11] 4,366,207

[45] Dec. 28, 1982

[54] POLYCARBONATE RESINS STABILIZED WITH NITRILES CONTAINING A 2-OH BENZOPHENONE GROUP

[75] Inventor: Blair T. Anthony, Schenectady, N.Y.

[73] Assignee: General Electric Company, Schenectady, N.Y.

[21] Appl. No.: 375,524

[22] Filed: May 6, 1982

Related U.S. Application Data

[63] Continuation-in-part of Ser. No. 241,993, Mar. 9, 1981, abandoned.

[51] Int. Cl.$^3$ .................... C08K 5/16; C07C 121/72
[52] U.S. Cl. ........................... 428/412; 260/465 D; 524/205; 524/208
[58] Field of Search .............. 260/465 D; 524/205, 524/208; 428/412

[56] References Cited

U.S. PATENT DOCUMENTS

| | | | |
|---|---|---|---|
| 3,215,725 | 11/1965 | Strobel et al. | 260/465 D |
| 3,391,110 | 7/1968 | Coleman | 524/338 |
| 3,462,475 | 8/1969 | Strobel et al. | 260/465 D |
| 3,582,398 | 6/1971 | Ringler | 428/412 |
| 3,617,330 | 11/1971 | Pellstocker | 428/412 |
| 3,843,390 | 10/1974 | Hudson et al. | 428/412 |

FOREIGN PATENT DOCUMENTS 390070  12/1973  U.S.S.R. .................. 260/465 D

*Primary Examiner*—V. P. Hoke
*Attorney, Agent, or Firm*—Joseph T. Cohen; James C. Davis, Jr.

[57] ABSTRACT

Polycarbonate resins, can be stabilized against the adverse influence of UV light by incorporating either directly into the resin or by means of a coating on the surface of the resin, an effective amount of a certain class of cyano stabilizers.

19 Claims, No Drawings

POLYCARBONATE RESINS STABILIZED WITH NITRILES CONTAINING A 2-OH BENZOPHENONE GROUP

This invention is a Continuation-in-part of application Ser. No. 241,993, filed Mar. 9, 1981, now abandoned, and is concerned with stabilized polycarbonate resinous compositions, comprising an admixture either directly incorporated into the polymer or as a coating on the surface of said resin, an effective amount of a class of cyano stabilizers (hereinafter so designated) of the formulas

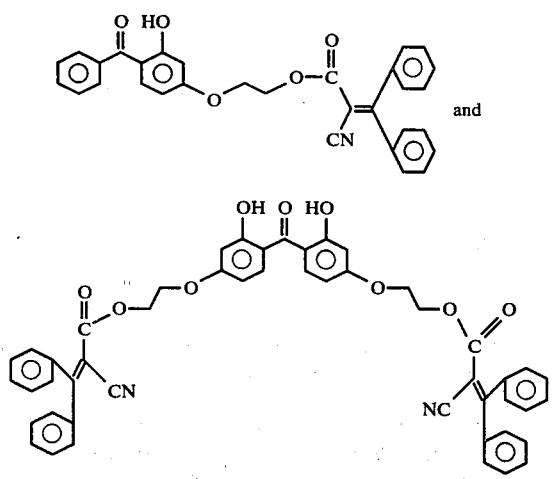

Polycarbonate polymers are excellent molding materials since products made therefrom have high impact strength, toughness, high transparency, wide temperature limits, and good dimensional stability. In particular, polycarbonate resins in the form of film or sheet materials in varying thicknesses, for instance, as protective film or for glazing purposes, have been extensively used because of the foregoing properties inherent in the polycarbonate resin. However, such polycarbonate resins are deficient in their ability to resist the effects of UV light which causes the polycarbonate resin to become colored and yellow under the continuing influence of UV light. Various UV stabilizers have been used in combination with polycarbonate resins to reduce the effect of coloring induced by UV light with varying success. One of the problems of using the usual UV stabilizer is that in molding the polycarbonate resin at elevated temperatures with the UV stabilizer therein, because of the higher volatility of usual stabilizers, losses of the stabilizer occur during the molding or film forming cycle, thereby reducing the stabilizer content with concomitant reduction in resistance to UV light. Moreover, even some of the more prominent UV stabilizers when incorporated in polycarbonate resins are unable to prevent yellowing of the polycarbonate resin being subjected to UV light for extended periods of time.

Unexpectedly, I have discovered that a certain class of stabilizers of formulas I and II can be incorporated in a polycarbonate resin in relatively small amounts or can be applied to the surface of any film or sheet materials made from such polycarbonate resin, either by itself or dispersed in the form of either a coating derived from the polycarbonate resin or a coating derived from another resin, such as polymethacrylate resin (which coatings can be applied in relatively thin coatings with the cyano stabilizer therein) to give marked improvements in resistance to UV light and in reduction in the loss of the stabilizer at elevated temperatures.

The UV stabilizers of formulas I and II employed in the practice of the present invention can be prepared in a tetrahydrofuran (THF) solvent in accordance with the equations shown below. The stabilizer of formula I can be prepared according to the equation

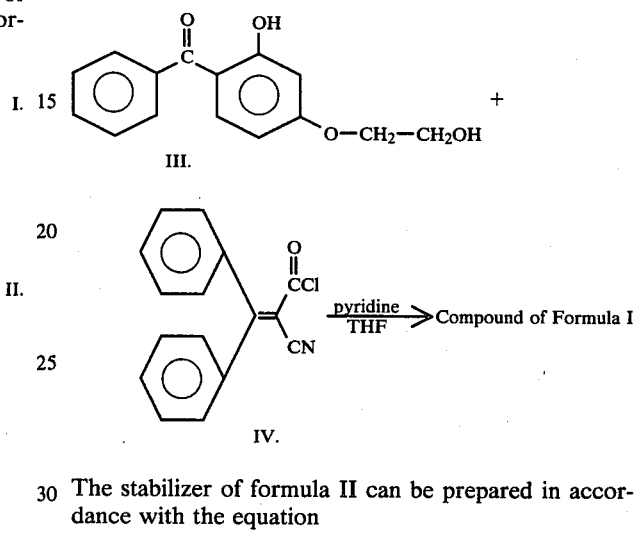

The stabilizer of formula II can be prepared in accordance with the equation

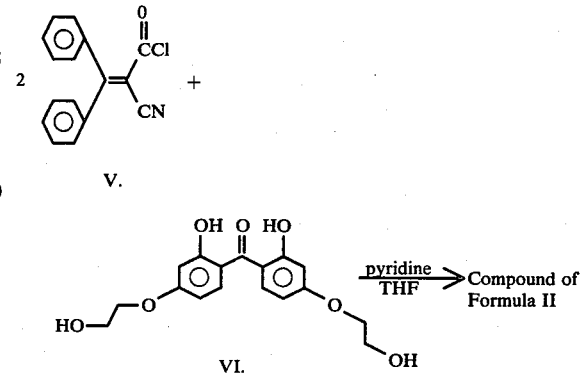

The compound of formula IV can be prepared by hydrolyzing a compound of the formula

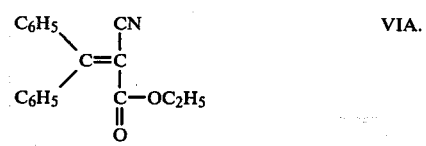

(also known as Uvinul N-35 manufactured by General Aniline) to the acid to give the compound of the formula

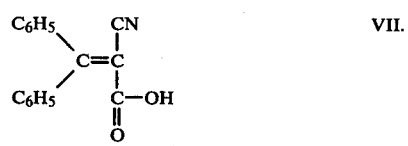

which when reacted with $SOCl_2$ (thionyl chloride) gives the compound of formula IV. The compound of formula VI and methods for preparing the same can be found disclosed in U.S. Pat. Nos. 3,644,466 issued Feb. 22, 1972 and 3,180,855 issued Apr. 27, 1965.

The dihydroxy compound of formula III required to make the stabilizer of formula I is obtained by reacting a commercial stabilizer known as Uvinul 400 manufactured by General Aniline and having the formula

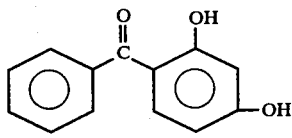   VIII.

with ethylene chlorohydrin in a sodium hydroxide solution to form the compound of formula I (as shown in U.S. Pat. No. 3,391,110).

The tetrahydroxy compound of formula VI required to make the stabilizer of formula II can be obtained (in accordance with the disclosures of the aforesaid U.S. Pat. No. 3,391,110) by reacting a commercial stabilizer known as Uvinul D-50 also made by General Aniline Company having the formula

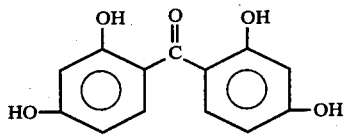   IX.

with ethylene chlorohydrin in a potassium hydroxide solution to form the compound of formula VI. By reacting the compound of either formula III or the compound of formula VI with the cyano derivative of formula IV in the required molar concentration as prescribed in the above-identified equations at temperatures ranging from 20° to 50° in the presence of pyridine as a hydrohalide acceptor, and THF as a solvent, one will obtain the desired stabilizers of formulas I and II.

In U.S. Pat. No. 3,462,475, Strobel, substituted cinnamic acid amides are described as UV stabilizers. No stabilizers of the cyanoacrylate or hydroxybenzophenone type used in the present invention are disclosed or taught. Strobel also states that ether linkages on his cinnamic acid ring system are detrimental to the UV stabilizing effect while ester linkages are not detrimental. These statements by Strobel may be true in this patent because the ether group will make the ring electron rich and shift the stabilizers UV spectra to longer more yellow wavelengths, while the ester linkage will remove electron density from the ring and shift the UV spectra to shorter wavelengths. The effects seen in my stabilizers are exactly the reverse as seen in the Strobel system. In my stabilizers, the ether linkage has no effect on shifting the UV spectra of the hydroxybenzophenone UV stabilizer. However, when an ester linkage is on the ring, too much conjugation results and the UV is shifted to longer wavelengths and to yellow color which is highly undesirable for UV stabilizers.

Russian Pat. No. 390070, (which is in the file of the parent case) which describes a stabilizer containing an ester linkage on the hydroxybenzophenone ring results in stabilizers greatly inferior to stabilizers employed by me. This superior performance of my stabilizers is surprising because of the presence of an ether linkage on the hydroxybenzophenone ring of my stabilizers. The advantages of my stabilizers over the Russian stabilizer are due to the fact that the Russian stabilizers undergoes a photo-Fries rearrangement upon exposure to UV light to give a highly conjugated yellow product as shown below.

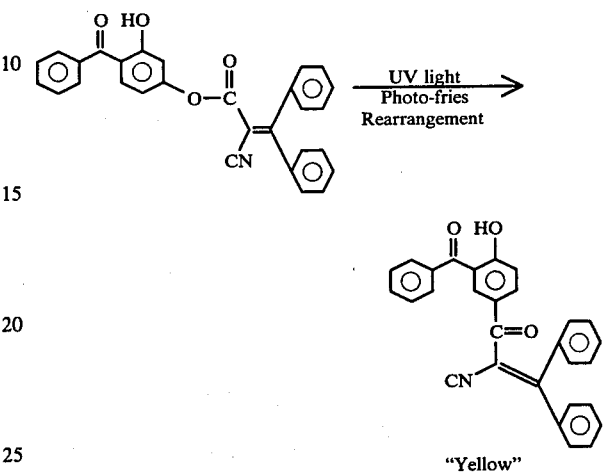

"Yellow"

It can thus be seen that the Russian compound provides no beneficial results over commercially available dihydroxybenzophenone.

The stabilizers used by me, because of the presence of the ether linkage (O ∾ O—) on the hydroxybenzophenone ring, do not undergo photo-Fries rearrangements to yellow products and are, therefore, superior UV stabilizers.

Strobel U.S. Pat. No. 3,215,725 discloses a dimeric cyanoacrylate UV stabilizer having the formula, e.g.,

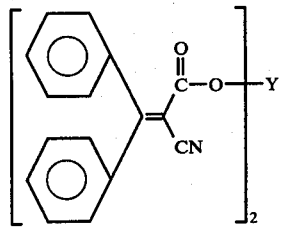

where Y is a non-chromophoric bridging radical, such as an alkylene radical, shown on the top of column 3 of the patent. Here Strobel is describing a dimeric monochromphoric UV stabilizer and no bichromophoric UV stabilizer is shown or taught combining a hydroxybenzophenone UV stabilizer with a cyanoacrylate UV stabilizer disclosed and claimed in my application.

Coleman U.S. Pat. No. 3,391,110 discloses one of the starting materials used for making my stabilizers as shown here.

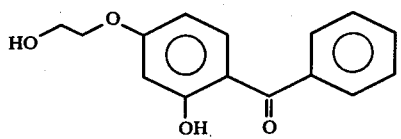

Coleman uses this stabilizer as a monomer to make polymeric UV stabilizers and does not in any way disclose or teach reacting this compound with any other UV stabilizer required to produce the stabilizers of my invention.

It is critical that one understand the chemistry involved in connection with these stabilizers. I am using novel bichromophoric stabilizers which are far superior as far as is known.

The aromatic polycarbonate resins which can be employed in the practice of the present invention are homopolymers and copolymers and mixtures thereof which have an intrinsic viscosity (I.V.) of 0.30 to 1.0 dl./g. or more as measured in methylene chloride at 25° C. and are prepared by reacting a dihydric phenol with a carbonate precursor. Typical of some of the dihydric phenols that may be employed in the practice of this invention are bisphenol-A [2,2-bis(4-hydroxyphenyl) propane], bis (4-hydroxyphenyl) methane, 2,2-bis (4 hydroxy-3-methylphenyl) propane, 4,4-bis(4-hydroxyphenyl) heptane, 2,2-(3,5,3',5'-tetrachloro-4,4'-dihydroxydiphenyl) propane, 2,2-(3,5,3',5'-tetrabromo-4,4'-dihydroxydiphenyl)-propane, (3,3'-dichloro-4,4'-dihydroxydiphenyl) methane, etc. Other dihydric phenols of the bisphenol type are also available and are disclosed in U.S. Pat. Nos. 2,999,835, 3,028,365 and 3,334,154.

It is, of course, possible to employ two or more different dihydric phenols for making copolymers of a dihydric phenol with a glycol or with a hydroxy or acid terminated polyester, or with a dibasic acid in the event a carbonate copolymer or inter-polymer rather than a homopolymer is desired for use in the preparation of the aromatic carbonate polymers of this invention. Also employed in the practice of this invention may be blends of any of the above materials to provide the aromatic carbonate polymer.

The carbonate precursor may be either a carbonyl halide, a carbonate ester or a haloformate. The carbonyl halides can be employed herein are carbonyl bromide, carbonyl chloride and mixtures thereof. Typical of the carbonate esters which may be employed herein are diphenyl carbonate, di-(halophenyl) carbonates such as di-(chlorophenyl) carbonate, di-(bromophenyl) carbonate, di-(trichlorophenyl) carbonate, di-(tribromophenyl) carbonate, etc. di-(alkylphenyl) carbonates such as di-(tolyl) carbonate, etc., di-(naphthyl) carbonate, di-(chloronaphthyl) carbonate, phenyl tolyl carbonate, chlorophenyl chloronaphthyl carbonate, etc. or mixtures thereof. The haloformates suitable for use herein include bis-haloformates of dihydric phenols (bischloroformates of hydroquinones, etc.) or glycols (bishaloformates of ethylene glycol, neopentyl glycol, polyethylene, glycol, etc.). While other carbonate precursors will occur to those skilled in the art, carbonyl chloride, also known as phosgene, is preferred.

Also included are the polymeric derivatives of a dihydric phenol, a dicarbonxylic acid and carbonic acid. These are disclosed in U.S. Pat. No. 3,169,121 which is incorporated herein by reference.

The aromatic carbonate polymers of this invention may be prepared by employing a molecular weight regulator, an acid acceptor and a catalyst. The molecular weight regulators which can be employed in carrying out the process of this invention include monohydric phenols such as phenol, chroman-I, paratertiarbutylphenol, parabromophenol, primary and secondary amines, etc. Preferably, phenol is employed as the molecular weight regulator.

A suitable acid acceptor may be either an organic or an inorganic acid acceptor. A suitable organic acid acceptor is a tertiary amine and includes such materials as pyridine, triethylamine, dimethylaniline, tributylamine, etc. The inorganic acid acceptor may be one which can be either a hydroxide, a carbonate, a bicarbonate, or a phosphate of an alkali or alkaline earth metal.

The catalysts which are employed herein can be any of the suitable catalysts that aid the polymerization of bisphenol-A with phosgene. Suitable catalysts include tertiary amines, such as, for example, teiethylamine, tripropylamine, N,N-dimethylaniline, quaternary ammonium compounds such as, for example, tetraethylammonium bromide, cetyl triethyl ammonium bromide, tetra-n-heptylammonium iodide, tetra-n-propyl ammonium bromide, tetramethylammonium chloride, tetramethyl ammonium hydroxide, tetra-n-butyl ammonium iodide, benzyltrimethyl ammonium chloride and quaternary phosphonium compounds such as, for example, n-butyltriphenyl phosphonium bromide and methyltriphenyl phosphonium bromide.

Also, included herein are branched polycarbonates wherein a polyfunctional aromatic compound is reacted with the dihydric phenol and carbonate precursor to provide a thermoplastic randomly branched polycarbonate.

These polyfunctional aromatic compounds contain at least three functional groups which are carboxyl, carboxylic anhydride, haloformyl or mixtures thereof. Examples of these polyfunctional aromatic compounds which may be employed in the practice of this invention include: trimellitic anhydride, trimellitic acid, trimellityl trichloride, 4-chloroformyl phthalic anhydride, pyromellitic acid, pyromellitic dianhydride, mellitic acid, mellitic anhydride, trimesic acid, benzophenonetetracarboxylic acid, benzophenonetetracarboxylic anhydride and the like. The preferred polyfunctional aromatic compounds are trimellitic anhydride or trimellitic acid or their haloformyl derivatives. Also, included herein are blends of a linear polycarbonate and a branched polycarbonate.

In order that those skilled in the art might better understand how the present invention may be practiced, the following examples are given by way of illustration and not by way of limitation. All parts are by weight unless otherwise indicated.

EXAMPLE 1

This example illustrates the preparation of the UV-stabilizer of formula I. More particularly, 5.2 grams (0.02 mol) of compound III was dissolved in 30 ml. pyridine. A solution of 5.8 grams (0.021 mol) of the cyano compound of formula IV in 50 cc dry THF (tetrahydrofuran) was added dropwise at room temperature of abour 25°-30° C. This mixture was allowed to react with stirring at 50° C. for about 20 hours. The solvent was removed by roto evaporation and the viscous oil obtained was dissolved in a 50/50 (weight percent) chloroform/hexane solution and passed through a silica gel column to remove any impurities. After roto evaporating off the solvent, the pure compound of formula I was obtained. The identity of the compound was established by NMR analysis.

EXAMPLE 2

This example illustrates the preparation of the UV-stabilizer of formula II. More particularly, 1.68 grams (0.005 mol) of the compound of formula VI was dissolved in 30 ml pyridine. Thereafter a solution of 2.7 grams (0.01 mol) of the cyano compound of formula V in 50 cc dry THF was added dropwise at ambient temperature (room temperature). The mixture was allowed to stir for 24 hours at 50° C. The reaction mixture was then worked up by washing first with 5% aqueous HCl, then with 5% aqueous sodium bicarbonate solution and finally with water. The organic solution which separated out was dried over magnesium sulfate and after filtration and solvent removal, crystals were obtained melting at 108°–111° C. The identity of the stabilizer of formula II was established by means of NMR analysis.

EXAMPLE 3

A 21.5 weight percent solid solution employing a polymethylmethacrylate resin dissolved in butyl cellosolve was prepared. This polymethylmethacrylate resin solution containing 3%, by weight, of either the monocyano compound of formula I or the dicyano compound of formula II, based on the weight of the methacrylate resin, was flowcoated onto a polycarbonate resin sheet and allowed to drain vertically for 30 minutes at room temperature before being cured in a vented oven for 1 hour at 125° C. This also removed the solvent. The measured thickness of the cured coating on the polycarbonate resin was about 0.30 mil.

EXAMPLE 4

This example shows the effect of the rate of photoaging of samples which were evaluated under a reflector sunlamp (RS) which were kept 8 inches above the samples which were being spun on a turntable (about 10 revolutions per minute) in a vented hood at 30° C. The yellowing index (YI) of the samples was periodically measured on an XL-20 Digital Tristimulus Calorimeter. The rate of photoaging of the samples containing the UV stabilizers of formulas I and II was greatly reduced as compared to other commercial stabilizers (Uvinul N-539 and Uvinul 531, both manufactured by General Aniline Company, and Cyasorb 5411, manufactured by the American Cyanamide Company as shown in the following Table I.

TABLE I

| Stabilizer | Initial YI | ΔYI 168 hrs. | 504 hrs. | 840 hrs. | 1008 hrs. |
|---|---|---|---|---|---|
| Uvinul N-539 | 1.4 | 1.1 | 3.4 | 4.6 | 5.0 |
| Uvinul 531 | 1.2 | 2.3 | 7.3 | 8.8 | 9.2 |

TABLE I-continued

| Stabilizer | Initial YI | ΔYI 168 hrs. | 504 hrs. | 840 hrs. | 1008 hrs. |
|---|---|---|---|---|---|
| Cyasorb 5411 | 1.0 | 2.4 | 6.2 | 7.4 | 8.0 |
| Compound I | 1.4 | 0.0 | 0.2 | 0.4 | 0.5 |
| Compound II | 1.4 | 0.2 | 0.2 | 0.5 | 0.8 |

EXAMPLE 5

In order to underline the stability of the cyano stabilizers of the instant invention as far as remaining in the thermoplastic polymer in which they are used as stabilizers, the following tests were conducted whereby the same amount of stabilizer deposited in the same polymethylmethacrylate resin flowcoated on a polycarbonate substrate and cured as in Example 3, was heated at 125° C. to determine how much of the stabilizer still remained after various periods of heating at this temperature. The following Table II shows the results of such tests.

TABLE II

| Stabilizer 3% by Weight | 0 hr. | 1 hr. | 2 hrs. | 4 hrs. | 8 hrs. | 24 hrs. |
|---|---|---|---|---|---|---|
| Uvinul N-539 | 100% | 71% | 64% | 57% | 48% | 41% |
| Uvinul 531 | 100% | 88% | 83% | 76% | 71% | 61% |
| Cyasorb 5411 | 100% | 68% | 62% | 51% | 45% | 42% |
| Compound I | 100% | 94% | 94% | 94% | 94% | 94% |
| Compound II | 100% | 95% | 95% | 95% | 95% | 95% |

It can be seen from the data in the aforesaid Table I that when either of the applicant's cyano stabilizers is used in combination with the aromatic polycarbonate resin, the resulting polycarbonate composition has considerably better resistance to UV light, as evidenced by its resistance to yellowing, even after many hundreds of hours of being subjected to a UV source. Also, Table II shows that the applicant's stabilizers, at elevated temperature, remain more permanently in the thermoplastic resin than other well known stabilizers.

EXAMPLE 6

In order to establish the unexpected advantages of using my stabilizer and the importance of the presence of the ether linkage between the benzophenone radical and the cyano-containing radical and particularly the disadvantage of using the stabilizer described in the aforesaid Russian patent and the advantage of using my stabilizers over the Russian stabilizer, the following example illustrates the results of using 2,4-dihydroxybenzophenone which is a commercially used stabilizer, one of the Russian ester stabilizers attached to the hydroxybenzophenone nucleus, and the stabilizer employed by me. In each instance, the stabilizer was applied to a polycarbonate resin similarly as was done in Example 3 and tests were conducted on the coated polycarbonate resin in the manner described in Example 4, with results shown in the following Table 3.

TABLE 3

| UV Stabilizer | Initial YI | ΔYI After R.S. Sunlamp Exposure | | | | | |
|---|---|---|---|---|---|---|---|
| | | 168 Hrs | 336 Hrs | 504 Hrs | 672 Hrs | 840 Hrs | 1008 Hrs |
| 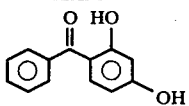<br>2,4-Dihydroxybenzophenone* | 1.5 | 2.4 | — | 4.2 | 5.8 | 6.9 | 7.8 |
| 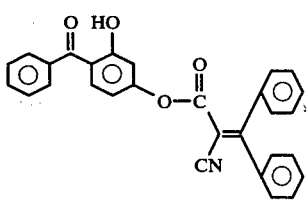<br>Russian ester stabilizer | 1.1 | 2.7 | — | 3.7 | 4.7 | 6.1 | 7.5 |
| 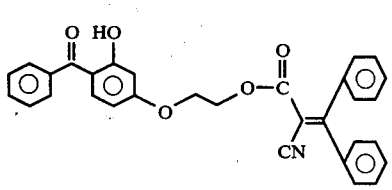<br>Stabilizer of present invention | 1.4 | 0.0 | 0.1 | 0.2 | 0.3 | 0.4 | 0.5 |

*Commercial UV Stabilizer.

It will be seen from the results described in Table 3 that one of the stabilizers employed in the practice of my invention when compared to either the 2,4-dihydroxybenzophenone, namely, the commercial UV stabilizer or even the Russian stabilizer, remained fairly low and constant over a period of 1,008 hours, whereas the other two stabilizers began to show an increase in the ΔYI after exposure to the sunlamp. Finally, whereas after 1008 hours, the stabilizer employed in the practice of my invention showed a ΔYI of only 0.5, the commercial UV stabilizer showed a ΔYI of 7.8 and the Russian stabilizer showed a ΔYI after sunlamp exposure of 7.5, which showed that my stabilizer is in the neighborhood of 15 times better than that of either the commercial stabilizer or that of the Russian stabilizer.

It will of course be apparent to those skilled in the art that in addition to the proportions of UV stabilizer incorporated, other proportions may be used with satisfactory results. Thus I can use from 0.5 to 10%, by weight, of the compounds of formulas I and II, based on the weight of the resin being stabilized.

The UV stabilizers of formulas I and II can be milled into the polycarbonate resin so that they are intimately dispersed throughout the latter to provide their stabilizing effect. Alternatively, instead of using the polymethacrylate resin for dispersing the UV stabilizers and applying them as thin coatings on the surface of the polycarbonate resin, other resins may be used as dispersing media for the UV stabilizers such as the polycarbonate resin itself and then applied as a thin coating over the substrate polycarbonate, which can range from 0.1 to 50 mils or more in thickness, especially when used for glazing purposes. Because of the high temperature stability of the UV stabilizers and their very low volatility, the polycarbonate substrate and the resinous medium in which the UV stabilizers are dispersed for positioning on the surface of the polycarbonate substrate, can advantageously be co-extruded at elevated temperatures using equipment readily available for the purpose, to effect a close bond between the upper layer containing the UV stabilizer and the substrate polycarbonate resin.

What I claim as new and desired to obtain by Letters Patent of the United States is:

1. A composition of matter comprising (1) a polycarbonate resin susceptible to degradation by ultraviolet light and (2) an effective amount of a UV stabilizer selected from the class consisting of

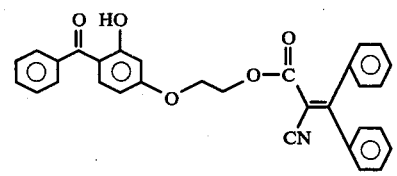

and

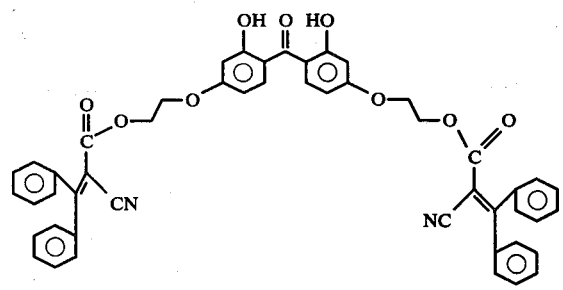

2. A composition of matter comprising (1) a polycarbonate resin susceptible to degradation by ultraviolet light and (2) an effective amount of a UV stabilizer comprising a compound having the formula

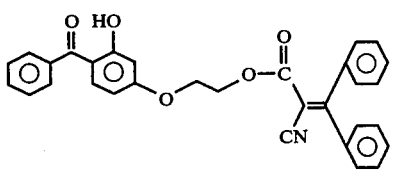

3. A composition of matter comprising (1) a polycarbonate resin susceptible to degradation by ultraviolet light and (2) an effective amount of a UV stabilizer comprising a compound having the formula

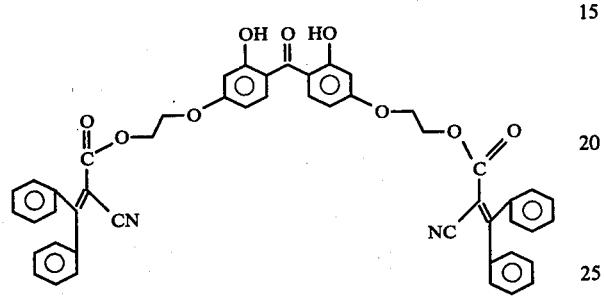

4. A composition as in claim 1 wherein the UV stabilizer is present in an amount ranging from 0.5 to 10%, by weight, based on the weight of the polycarbonate resin.

5. A composition as in claim 2 wherein the polycarbonate resin is in the form of a film or thick sheet.

6. A composition as in claim 3 wherein the poly carbonate resin is in the form of a film or thick sheet.

7. A composition as in claim 2 wherein the UV stabilizer is homogeneously dispersed throughout the polycarbonate resin.

8. A composition as in claim 3 wherein the UV stabilizer is homogeneously dispersed throughout the polycarbonate resin.

9. A composition as in claim 2 wherein the polycarbonate resin being protected against the effects of ultraviolet light is so protected by means of a thin coating of a resinous composition containing the UV stabilizer dispersed homogeneously throughout the thin coating, which in turn is disposed on the surface of the polycarbonate substrate.

10. A composition as in claim 3 wherein the poly carbonate resin being protected against the effects of ultraviolet light is so protected by means of a thin coating of a resinous composition containing the UV stabilizer dispersed homogeneously throughout the thin coating, which in turn is disposed on the surface of the polycarbonate substrate.

11. A compound of the formula

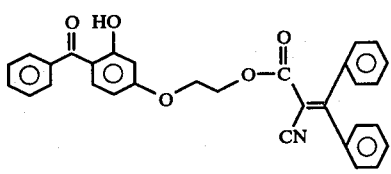

12. A compound of the formula

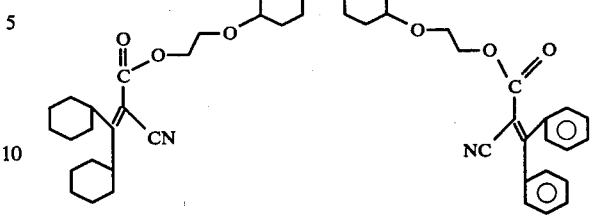

13. A composition selected from the class consisting of

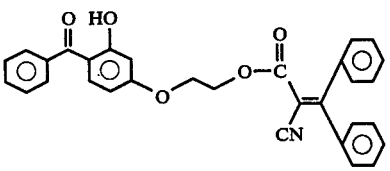

and

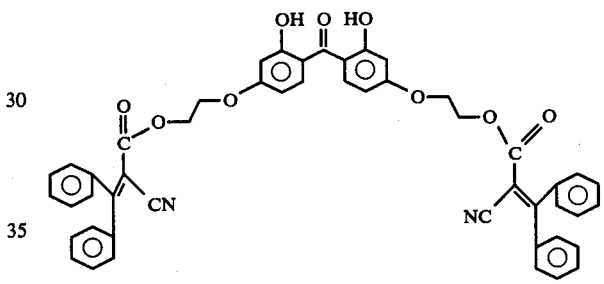

14. The method for improving the U-V stability of polycarbonate resins susceptible to degradation by ultraviolet light which comprises incorporating in said polycarbonate resin an effective amount of a UV-stabilizer selected from the class consisting of:

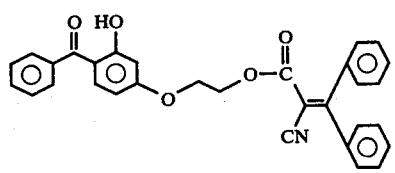

and

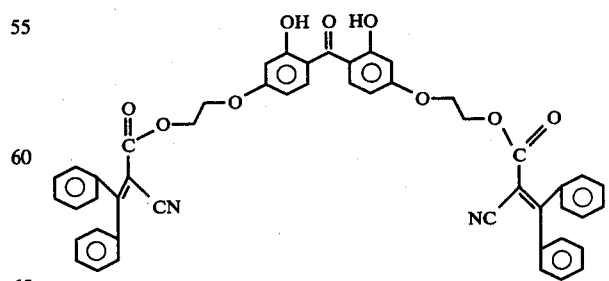

15. The process as in claim 14, wherein the stabilizer is:

16. The process as in claim 14 wherein the stabilizer is:

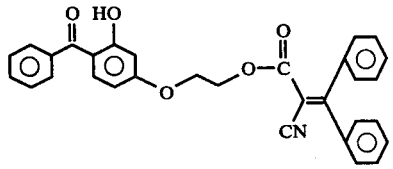

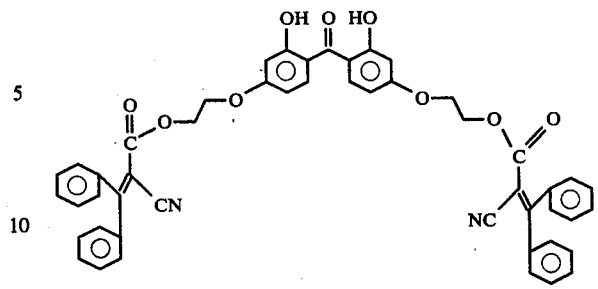

17. The process as in claim 14 wherein the stabilizer is incorporated in an amount ranging from 0.5 to 10%, by weight, based on the weight of the polycarbonate resin.

18. The process as in claim 14 wherein the UV stabilizer is homogeneously dispersed throughout the polycarbonate resin.

19. The process as in claim 14 wherein the polycarbonate resin being protected against the effects of ultraviolet light is so protected by means of a thin coating of a resinous composition containing the UV stabilizer dispersed homogeneously throughout the thin coating which in turn is disposed on the surface of the polycarbonate substrate.

* * * * *